United States Patent
Simoneau-Buessinger et al.

(10) Patent No.: US 10,835,173 B2
(45) Date of Patent: Nov. 17, 2020

(54) ANKLE ERGOMETER

(71) Applicants: UNIVERSITE DE VALENCIENNES ET DU HAINAUT-CAMBRESIS, Valenciennes (FR); CENTRE NATIONAL DE LA RECHERCHE SCIENTIFIQUE—CNRS, Paris (FR)

(72) Inventors: Emilie Simoneau-Buessinger, Prouvy (FR); Christophe Gillet, Semousies (FR); Sebastien Leteneur, Erre (FR); Jean-Francois Debril, Poitiers (FR); Nicolas Decoufour, Fouquieres lez Bethune (FR)

(73) Assignees: UNIVERSITE DE VALENCIENNES ET DU HAINAUT—CAMBRESIS, Valenciennes (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 136 days.

(21) Appl. No.: 15/544,742

(22) PCT Filed: Dec. 17, 2015

(86) PCT No.: PCT/FR2015/053578
§ 371 (c)(1),
(2) Date: Jul. 19, 2017

(87) PCT Pub. No.: WO2016/116673
PCT Pub. Date: Jul. 28, 2016

(65) Prior Publication Data
US 2018/0014775 A1    Jan. 18, 2018

(30) Foreign Application Priority Data
Jan. 20, 2015  (FR) ...................... 15 50439

(51) Int. Cl.
A61B 5/103    (2006.01)
A61B 5/00     (2006.01)
(Continued)

(52) U.S. Cl.
CPC .......... *A61B 5/4595* (2013.01); *A61B 5/1107* (2013.01); *A61B 5/221* (2013.01);
(Continued)

(58) Field of Classification Search
CPC ..... A61B 5/4595; A61B 5/4519; A61B 5/221; A61B 5/6828; A61B 5/1107; A61B 5/702;
(Continued)

(56) References Cited

U.S. PATENT DOCUMENTS

2004/0186399 A1* 9/2004 Tseng ................ A61H 15/0078
                                                              601/112
2007/0142190 A1* 6/2007 Yeh ..................... A63B 21/0083
                                                              482/112

(Continued)

OTHER PUBLICATIONS

Reeves, Neil D., et al. "Influence of 90-day simulated microgravity on human tendon mechanical properties and the effect of resistive countermeasures." Journal of applied physiology (2005) (Year: 2005).*

(Continued)

*Primary Examiner* — Navin Natnithithadha
*Assistant Examiner* — Andrey Shostak
(74) *Attorney, Agent, or Firm* — Nixon & Vanderhye

(57) ABSTRACT

Disclosed is an ankle ergometer for measuring a force exerted on a user's ankle joint by muscles involved in ankle mobility, including: a first splint-type portion receiving the lower limb when the user's knee is extended, and including a lower limb immobilizer with the leg in extension, and a second portion including: a) a main body attached to the first (Continued)

portion, b) a counter-supporting unit secured to the main body, c) a rigid plate forming a supporting surface for the lower surface of the foot, the rigid plate being substantially static relative to the counter-supporting unit, d) a force sensor between the plate and the counter-supporting unit, the plate not being secured to the main body so the sensor measures the force exerted on the supporting surface of the plate by the ankle mobility muscles, the force being transmitted from the plate to the counter-supporting unit.

12 Claims, 4 Drawing Sheets

(51) Int. Cl.
*A61B 5/11* (2006.01)
*A61B 5/22* (2006.01)

(52) U.S. Cl.
CPC ............ *A61B 5/224* (2013.01); *A61B 5/4519* (2013.01); *A61B 5/6828* (2013.01); *A61B 5/6829* (2013.01); *A61B 5/702* (2013.01); *A61B 5/1124* (2013.01); *A61B 5/4023* (2013.01)

(58) Field of Classification Search
CPC ..... A61B 5/6829; A61B 5/224; A61B 5/4023; A61B 5/1124
See application file for complete search history.

(56) References Cited

U.S. PATENT DOCUMENTS

| | | | |
|---|---|---|---|
| 2011/0040225 A1* | 2/2011 | Gibbons | A61F 5/0127 602/23 |
| 2011/0160625 A1* | 6/2011 | Yefimov | A61H 1/0259 601/5 |
| 2011/0256983 A1* | 10/2011 | Malack | A61H 1/0266 482/4 |
| 2012/0010534 A1 | 1/2012 | Kubiak et al. | |
| 2012/0277063 A1* | 11/2012 | Zhang | A61B 5/4595 482/8 |
| 2013/0303947 A1 | 11/2013 | Gamet et al. | |

OTHER PUBLICATIONS

International Search Report, dated Apr. 22, 2016, from corresponding PCT/FR2015/053578 application.
Haxton, "Absolute Muscle Force in the Ankle Flexors of Man," J. Physiol., vol. 103, 1944, pp. 267-273.
Simoneau, et al., "Difficult Memory Task During Postural Tasks of Various Difficulties in Young and Older People: A Pilot Study," Clinical Neurophysiology, vol. 119, 2008, pp. 1158-1165.
Simoneau, et al., "Antagonist Mechanical Contribution to Resultant Maximal Torque at the Ankle Joint in Young and Older Men," Journal of Electromyography and Kinesiology, vol. 19, 2009, pp. e123-e131.
Billot, et al., "Age-Related Relative Increases in Electromyography Activity and Torque According to the Maximal Capacity During Upright Standing," Eur. J. Appl. Physiol., vol. 109, 2010, pp. 669-680.
Tognella, et al., "A Mechanical Device for Studying Mechanical Properties of Human Muscles In Vivo," J. Biomechanics., vol. 30, No. 10, 1997, pp. 1077-1080.
Ochala, et al., "Changes in Mechanical Properties of Human Plantar Flexor Muscles in Ageing," Experimental Gerontology, vol. 39, 2004, pp. 349-358.
Reeves, et al., "Influence of 90-day Simulated Microgravity on Human Tendon Mechanical Properties and the Effect of Resistive Countermeasures," J. Appl. Physiol, vol. 98, 2005, pp. 2278-2286.
Scaglioni, et al., "Plantar Flexor Activation Capacity and H Reflex in Older Adults: Adaptations to Strength Training," J. Appl. Physiol., vol. 92, 2002, pp. 2292-2302.
Ferri, et al., "Strength and Power Changes of the Human Plantar Flexors and Knee Extensors in Response to Resistance Training in Old Age," Acta Physiol Scand, vol. 177, 2003, pp. 69-78.
Cresswell, et al., "Influence of Gastrocnemius Muscle Length on Triceps Surae Torque Development and Electromyographic Activity in Man," Exp Brain Res, vol. 105, 1995, pp. 283-290.

* cited by examiner

ANKLE ERGOMETER

TECHNICAL FIELD AND PRIOR ART

The present invention relates to the field of ergometers, and more particularly that of ankle type ergometers.

One of the objects of the present invention is to provide a measurement apparatus able to measure with accuracy the mechanical properties of muscles of the ankle, and notably the capability of the muscles involved in the mobility of the ankle, and more particularly the capability of the muscles of the ankle of exerting a force for achieving plantar flexion (or extension) and/or dorsal flexion (or dorsiflexion).

The present invention finds many advantageous applications in the medical and/or paramedical field or further in the sports field for example during physical preparation.

As an example mention may be made of applications of the present invention, the conduction of tests on a person in order to evaluate his/her capability of maintaining an orthostatic posture (standing position); this is for example particularly advantageous in a medical context in order to allow a bedridden patient during an extended period to stand and to resume physical activity safely.

Other advantageous applications may also be contemplated within the scope of the present invention, such as for example for carrying out adapted rehabilitation exercises for the person for example subsequently to a sprain of the ankle, or further for evaluating the progress achieved by a person subsequently to a sprain of the ankle.

It is known that the neuromuscular system has the capability of modifying its characteristics and/or its behavior under the influence of endogenous and/or exogenous factors such as for example ageing, hypoactivity or further hyperactivity.

This phenomenon is known under the term of neuromuscular plasticity.

Thus, the capability of a muscle for producing a force may increase or decrease depending on its stress.

In order to evaluate this neuromuscular plasticity, there exist measurement instruments of the ergometer type which give the possibility of evaluating the impact of ageing, of extended immobilization or further of training; this is achieved on the basis of an analysis of the force moments developed at the joints.

If one is more particularly interested in the joint of the ankle, it is seen that the production of force on the joint of the ankle for an extension and a dorsiflexion of the foot is of particular importance, notably for maintaining an individual in equilibrium in an orthostatic posture.

FIG. 1 appended to the present description schematically illustrates a foot in plantar flexion P1 and in dorsiflexion P2.

These two main movements at the ankle (extension/dorsiflexion) are carried out in a sagittal plane around an axis transverse to the ankle.

The dorsiflexion P2 gives the possibility of approaching the back of the foot from the front face of the leg; the extension P1 moves the back away from the foot of the front face of the leg, causing the foot to be placed in the extension of the leg.

Thus, by allowing active extension P1 and dorsiflexion P2, the muscles around the joint of the ankle give the possibility of maintaining an individual in equilibrium in an orthostatic posture and also give the possibility of locomotion (walking, running and lateral displacements).

One therefore understands that it is very important, notably from a medical point of view of being able to evaluate accurately the mechanical and functional properties of the muscles of the ankle, and notably the forces (or force moments) produced by the muscles of the ankle in extension P1 and in dorsiflexion P2.

This notably gives the possibility of evaluating the capability of an individual to produce a sufficient muscular force for maintaining oneself in an orthostatic posture and/or resuming a physical activity.

Conventionally, the measurement apparatuses of the ergometer type include a pedal connected:

either to a unidirectional force sensor placed at a distance from the axis of rotation of the pedal, or to a torque sensor placed at the axis of rotation of the pedal (i.e. aligned with the flexion-extension rotation of the joint of the ankle).

These sensors are thereby configured for measuring the force or the force moment produced under static conditions.

This measurement is directly made with a torque sensor or indirectly with a force sensor.

For the force sensor, actually it must multiply the force measured by the lever arm between the axis of the pedal (ankle axis) and the axis of the force sensor (point of application of the force).

On the basis of this measurement technique, there exist several types of ergometers in the state of the art.

A first type of ergometer listed in the state of the art is illustrated in FIG. 2.

In this FIG. 2, a support S placed behind the back and the pelvis of the user U is distinguished so that the knee G of the user is in complete extension and that the sole of the foot P is in contact with a vertical plank PV.

This plank PV is jointed on the ground with a hinge system SC allowing pivoting of the plank relatively to the ground.

A force gauge D is moreover attached between this vertical plank PV and the support S for maintaining said plank in position in a substantially vertical axis when no force is exerted on the plank by the user.

This force gauge D is further configured for measuring the force exerted at the sole of the foot P subsequent to plantar flexion.

Such a system is described in "*Absolute muscle force in the ankle flexors of man.*" *J. Physiol.* (1944) 103, 267-273, Haxton, H. A. (1944).

Such a system only allows measurement of the forces exerted during plantar flexion (or extension), and does not allow measurement of the forces exerted during a dorsal flexion (or dorsiflexion).

There exist other types of ergometers.

For example the ergometer developed by the Institut Universitaire Technologique de Génie Mécanique of Dijon which gives the possibility of measuring the muscular moments at the joint of the ankle via a pedal with strain gauges.

With such an ergometer, the user should be in a sitting position with a hip substantially bent to 110°, a substantially bent knee to 120°, and an ankle to 90° (see notably Simoneau et al. 2008: "*Difficult memory task during postural tasks of various difficulties in young and older people: a pilot study.*" *Clin Neurophysiol* 119(5): 1158-65, or Simoneau et al. 2009: "*Antagonist mechanical contribution to resultant maximal torque at the ankle joint in young and older men.*" *J Electromyogr Kinesiol* 19(2): 123-31, or further Billot et al. 2010: "*Age-related relative increases in electromyography activity and torque according to the maximal capacity during upright standing.*" *Appl Physiol* 109(4): 669-80).

Further, the ergometer of the ankle type developed by Bio2M is further known.

This ergometer is specially designed for testing the mechanical properties of plantar flexor muscles at the joint of the ankle (see notably Tognella et al. 1997: "A mechanical device for studying mechanical properties of human muscles in vivo." J Biomech 30(10): 1077-80, or Ochala et al. 2004: "Changes in mechanical properties of human plantar flexor muscles in ageing." Exp Gerontol 39(3): 349-58), and notably for measuring the contractile properties of the muscles for example subsequent to isometric, isokinetic and isotonic contractions.

It consists of two main units:

(i) a power unit which notably contains an actuator and a torque sensor which are electronically connected together, and (ii) a control unit controlled by a computer.

According to this ergometer, the angular displacements of the ankle are measured with a digital optical sensor, and the angular velocities are taken from a resolver connected to the rotor, except for velocities greater than 15.70 rad·s$^{-1}$ which require a tachymeter.

The torques are obtained by using a torque sensor with gauges.

The user of such an ergometer should hold an elongated position on the back with the knee flexed to 120°.

Such an ergometer minimizes the contribution of the gastrocnemius muscles (see notably Cresswell et al. 1995: "Influence of gastrocnemius muscle length on triceps surae torque development and electromyographic activity in man." Exp Brain Res 105(2): 283-90); such muscles have their importance in plantar flexion and their contribution should not be minimized and set aside from the measurement if the intention is to have an accurate measurement.

An ergometer like the one illustrated in FIG. 3 is also known.

With such an ergometer, the measurements of the isometric force in plantar flexion are conducted with a stable attachment of the lower limb by blocking the joint of the knee to 90°, thereby minimizing the rotation of the joint of the ankle during the isometric contraction (notably see Reeves et al. 2005: "Influence of 90-day simulated microgravity on human tendon mechanical properties and the effect of resistive countermeasures." J Appl Physiol 98(6): 2278-86).

Finally, there exist several studies conducted on the joint of the ankle which use the "CybexNorm®" for evaluating the applied moments by the muscles of the ankle (see notably Scaglioni et al. 2002: "Plantar flexor activation capacity and H reflex in older adults: adaptations to strength training." J Appl Physiol 92(6): 2292-302, or Ferri et al. 2003: "Strength and power changes of the human plantar flexors and knee extensors in response to resistance training in old age." Acta Physiol Scand 177(1): 69-78).

The Applicant however submits that the whole of the existing ergometers of ankle type have many limits and many drawbacks.

Indeed, on most ergometers, the user may be supported on his/her back or on his/her shoulders for pushing more strongly on the pedal.

This necessarily implies the mobilization of muscles of other joints, which causes an overestimation of the evaluation of the forces or of the force moments developed at the ankle and may also cause strong variability of the measurements.

In other words, with the present ergometers, it is possible to record a force moment during plantar flexion, without using the muscles of the ankle responsible for plantar flexion.

This is due to the fact that with the present ergometers, the user may stress other muscles during the effort for achieving plantar flexion, for example the extensor muscles of the knee or of the hip: the configuration of the present ergometers therefore implies an error which is difficult to detect so that it is impossible to correct them a posteriori.

The ergometers of the ankle type which require positioning of the flexed knee to 90° try to limit the participation of these knee or hip extensor muscles.

However, these ergometers also reduce the stress of the gastrocnemius muscles during plantar flexion, as this is the case for example of the ergometer illustrated in FIG. 3.

Now, as mentioned above, the capability of producing force of these gastrocnemius muscles is important for evaluating the plantar flexion in the stretched leg position (in extension): indeed, these gastrocnemius muscles necessarily have to be taken into account for a specific and relevant measurement for a functional point of view, notably for reuse during the study of the orthostatic posture.

The Applicant moreover observes that the existing ergometers generally use a unidirectional force sensor or force moment sensor: such a sensor underestimates the resulting moments at the ankle: indeed, a plantar flexion (extension) and/or a dorsal flexion (dorsiflexion) are always accompanied by associated inversion and adduction movements, in two planes other than the sagittal plane.

The existing ergometers do not give the possibility of evaluating the whole of the exerted stresses at the joint of the ankle.

The use of a unidirectional sensor exclusively gives the possibility of determining what occurs around the transverse axis of the ankle; such a sensor does not give the possibility of evaluating the accessory moments to the plantar flexion, i.e. those around sagittal (or longitudinal) and vertical axes of the ankle (in inversion and in adduction).

Finally, the Applicant observes that the existing ergometers are often very bulky and difficult to displace; moreover, the existing ergometers can only be used on a single leg at a time and cannot be easily used in a bedridden position.

Object and Summary of the Present Invention

The present invention aims at improving the situation described above.

The present invention is directed to finding a remedy to the different drawbacks mentioned above by proposing an ergometer, not very bulky and inexpensive, which may measure accurately the forces exerted at the joint of the ankle by the flexor muscles of the foot of an individual and exclusively the forces exerted by these muscles, and not those exerted by other muscles such as the hip or knee extensor muscles.

For this purpose, the object of the present invention relates according to a first aspect to an ergometer of the ankle type for measuring the forces exerted on the joint of the ankle of a user by the muscles involved in the mobility of said ankle.

According to the present invention, the ergometer includes a first portion and a second portion, appearing as a boot.

Advantageously, the first portion is of the splint type; it is able to receive a lower limb of the user when the knee of the latter is in extension.

Advantageously, this first portion comprises immobilization means which are configured for immobilizing the lower limb with the knee in extension.

Advantageously, the second portion comprising:
a) a main body attached to the first portion,
b) a counter-supporting element secured to the main body,
c) a rigid plate forming a supporting surface for the lower surface of the foot when the lower limb is immobilized with the immobilization means, said rigid plate being substantially static relatively to said counter-supporting element,
d) a force sensor inserted between said plate and said counter-supporting element.

According to the invention, the plate is not secured to the main body so that the sensor is able to measure the force exerted on the supporting surface of the plate by the muscles involved in the mobility of said ankle, said force being transmitted from the plate to the counter-supporting element.

By static plate relatively to the counter-supporting element, it should be understood here that the plate does not move (from a macroscopic point of view) relatively to the counter-supporting element (notably for example when the user exerts a force with his/her foot on said plate).

By plate not secured with the main body, it should be understood here that the plate on which rests the foot of the user is structurally independent of the main body, and therefore of the counter-supporting element, the only link between both elements being the force sensor which is inserted between the plate and the counter-supporting element.

Thus, both by its structure and by its configuration, the ergometer designed within the scope of the present invention appears as a simple exercising apparatus in its use and accurate in the conducted measurements.

The layout of a sensor inserted between a counter-supporting element and a rigid free plate (not secured) and fixed (non-static) plate relatively to the counter-supporting element gives the possibility of having an accurate and reliable measurement of the force exerted by the flexor muscles of the foot (or plantar flexion muscles) and transmitted from the plate to the counter-supporting element.

Such a sensor notably gives the possibility of a use in a "closed chain".

It is sufficient to position at the level of the first portion of the ergometer, the leg with the knee in extension and then of immobilizing it with means provided for this purpose.

In this position, the foot is resting on the rigid plate.

It is then sufficient to exert a flexion force (either plantar or dorsal) on the plate.

This force will be transmitted to the counter-supporting element.

The force sensor, positioned between the plate and the counter-supporting element, may thus measure this force.

In order to measure the force exerted during plantar flexion and/or dorsal flexion of the foot of the user, it is advantageously provided that the force sensor is of the 3D sensor type (i.e. a three-dimensional sensor).

Preferably, the force sensor is a force moment sensor able to measure the forces and the force moments in three dimensions (3D).

In an advantageous embodiment, a use of the ergometer in a "open chain" is preferred.

In this embodiment, the ergometer further includes:
a rolling or sliding track,
a rolling or sliding member.

This rolling or sliding member is attached to the main body.

In an advantageous embodiment, this rolling or sliding member is substantially positioned at the heel of the boot. This member may be positioned elsewhere if required, notably for technical reasons.

Advantageously, the rolling or sliding member is able to cooperate with the rolling or sliding track in order to limit the friction between the main body and the track.

The presence of this member on the main body and the cooperation of this member with the track make the device independent of its environment.

This configuration in "open chain" thereby gives the possibility of measuring with great reliability and great accuracy, the force exerted by the muscles of the ankle: this configuration in an "open chain" avoids the measurement of the compensations of the muscles of the other joints.

Indeed, in this configuration, the presence of this member and of this rolling or sliding track avoids any friction which may give a support to the user for urging other muscles such as for example the hip extensor muscles.

In an alternative, the rolling or sliding member comprises a roller for rolling the main body relatively to the track.

Such a roller allows displacement of the body with respect to the track with a minimum of friction.

In an alternative embodiment, the rolling or sliding member comprises a planar contact surface and the rolling or sliding track comprises a plank having a plurality of beads uniformly distributed on the plank.

In this alternative, the rolling or sliding member may roll on the beads so as to move in all the directions of the plane of the plank with a minimum of friction.

Advantageously, the plate comprises at its lateral edges, stiffening elements; the latter extend perpendicularly relatively to the plate.

These stiffening elements reduce, or even suppress the possible deformations of the plate, for example during flexion of the foot.

Preferably, the immobilization means comprise a set of straps for maintaining immobilized the lower limb of the user.

Preferably, the second portion comprises a shoe for receiving the foot of the user, said shoe being attached on the plate so as to maintain the foot secured to the plate.

By means of such a shoe, the foot is secured to the plate.

Alternatively or additionally, a set of straps may also be provided for maintaining the foot.

Advantageously, the ergometer according to the present invention includes first so called angular adjustment means, which are configured for adjusting the angular position of the second portion relatively to the first portion.

Such adjustment means give the possibility of adjusting the tilt of the foot on the supporting surface of the plate.

Such an adjustment gives the possibility of evaluating the relationship between the tilt of the ankle and the developed forces.

In a particular embodiment, the adjustment means comprise:
a pair of retractable nuts positioned on the first portion, and
a plurality of adjustment holes made on the main body of the second portion.

In this embodiment, the nuts are able to be introduced into the adjustment holes for adjusting and locking the angular position of the second portion relatively to the first portion.

One skilled in the art will understand here that the above adjustment means may be more generally a locking system with springs able to cooperate with grooves made on the main body.

Advantageously, the ergometer according to the present invention includes second adjustment means, said to be in height, which are configured for adjusting the height of the first portion relatively to the second portion.

Such an adjustment in height gives the possibility of adjusting the ergometer depending on the size of the user, and notably the size of the leg of the user.

Advantageously, the ergometer according to the present invention includes a computer processing unit which is able to receive and process the measurement signals coming from the sensor in order to determine the force exerted by the muscles involved in the movements of the ankle.

Correlatively, the object of the present invention relates according to a second aspect to the use of an ergometer as described above for achieving predetermined rehabilitation exercises and adapted to the user.

Alternatively, the object of the present invention relates according to a third aspect to the use of an ergometer as described above for carrying out force tests on a person in order to evaluate the capability of this person of maintaining an orthostatic posture, notably for allowing a bedridden person to resume the standing position and/or an activity.

Thus, the object of the present invention, by its different functional and structural aspects described above, allows an accurate and reliable measurement of the force produced by the flexor and/or extensor muscles of the ankle, by limiting the influence of the forces exerted by other muscles, as is the case in the other ergometers developed until now.

SHORT DESCRIPTION OF THE APPENDED FIGURES

Other features and advantages of the present invention will become apparent from the description above, with reference to the appended FIGS. 4 to 6 which illustrate an embodiment thereof without any limitation and wherein:

FIG. 1 schematically illustrates a foot in plantar flexion P1 and in dorsiflexion P2.

Figure 1:
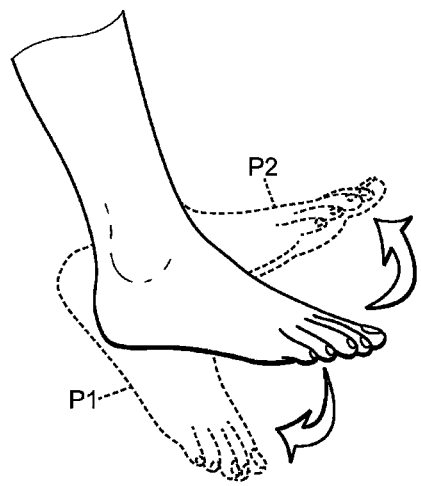
Figure 2:
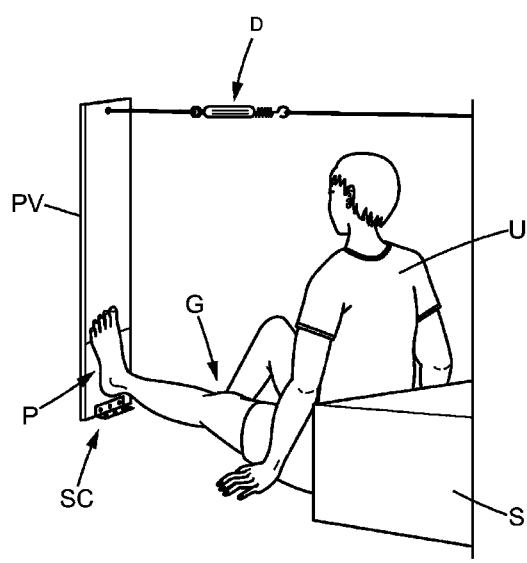
FIG. 2 shows a first prior art ergometer.
Figure 3:
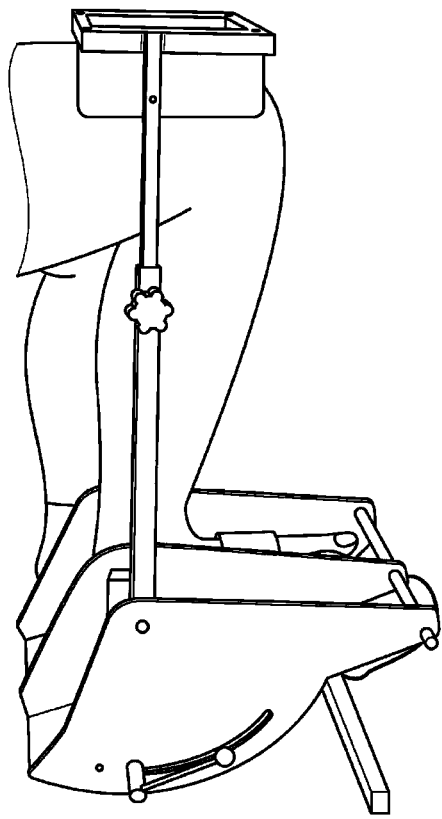
FIG. 3 shows a second prior art ergometer.
Figure 4:
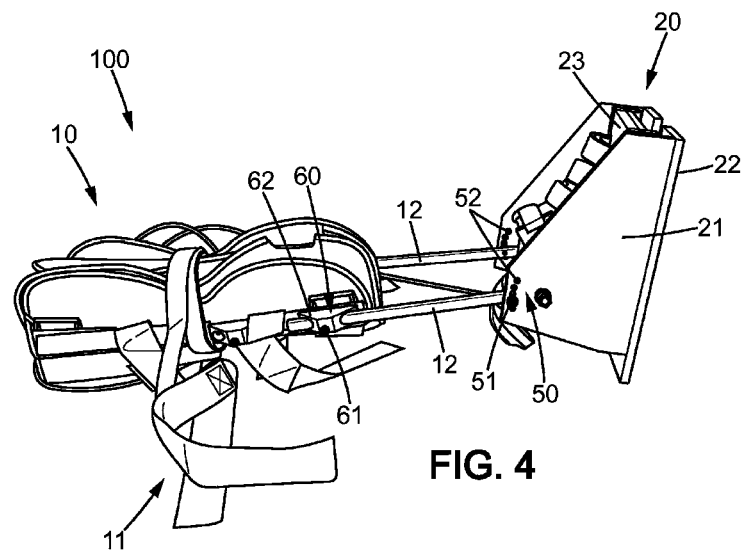
Figure 5:
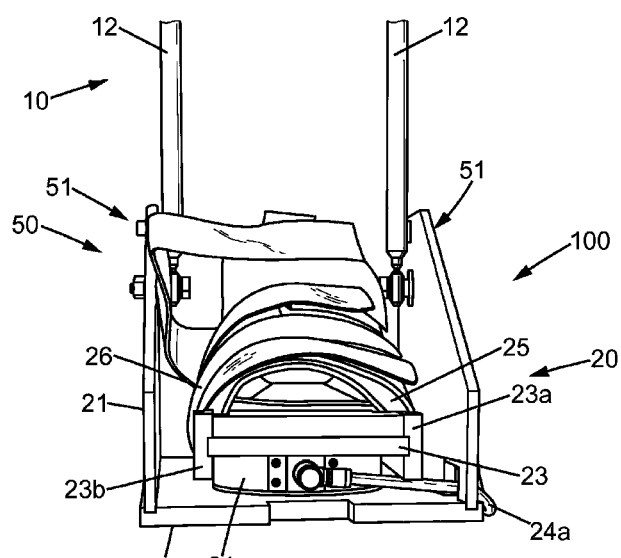
Figure 6:
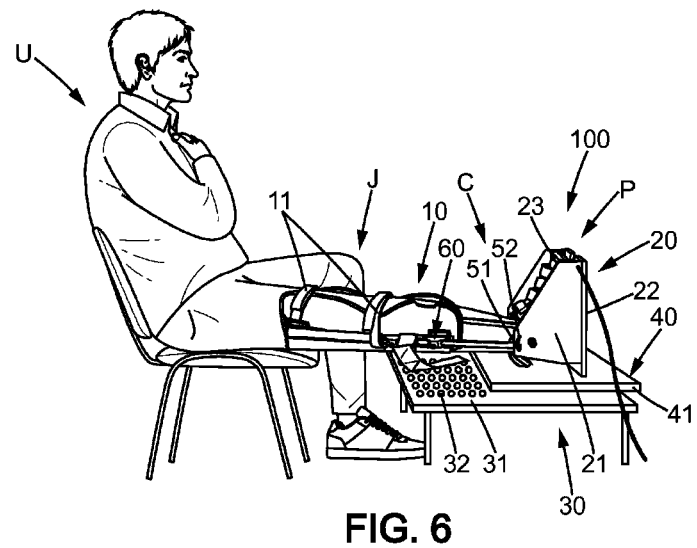

FIG. 4 schematically illustrates a lateral view of an ergometer according to an exemplary embodiment;

FIG. 5 schematically illustrates a front view of an ergometer according to FIG. 4;

FIG. 6 schematically illustrates a lateral view of an ergometer according to FIG. 4 with a rolling or sliding member and track.

DETAILED DESCRIPTION OF DIFFERENT EXEMPLARY APPLICATIONS

An ergometer according to an exemplary embodiment of the present invention will now be described in the following by referring jointly to FIGS. 4 to 6.

As a reminder, during the isometric contraction of the muscles of the ankle towards the extension, it is noted on most ergometers of the state of the art that the user uses the support of his/her back or of his/her shoulders for pushing on the pedal of the ergometer, which involves a participation of other muscles on other joints inducing an overestimation of the evaluation of the forces (or force moments) developed on the joint of the ankle.

It is also observed that the ergometers of the ankle type which position the user in the sitting position, with the knee bent to 90° in order to limit the participation of the joint of the knee, reducing the forces of the gastrocnemius muscles.

Now, it is important to evaluate the forces developed by these gastrocnemius muscles on the ankle.

It is therefore preferable to conduct the tests with the knee in extension for taking into account these forces.

One of the objects of the present invention is therefore to design an ergometer able to measure, in the position with the stretched leg (i.e. knee in extension), the maximum force developed by the flexor muscles and/or by the extensor muscles of the ankle; i.e. the muscles allowing stabilization of the ankle in the sagittal plane (plantar flexion and dorsiflexion).

This is made possible in the example which follows with an ergometer 100 of the ankle type like one illustrated in FIG. 4.

In the example described here, the ergometer 100 comprises a first portion 10 of the splint type.

In this example, this first portion 10 is a Zimmer splint: said splint is able to receive the lower limb of the user U when the knee of the user is in extension as illustrated in FIG. 6.

Of course, one skilled in the art will understand here that other types of splint may be used like for example a gutter-shaped splint receiving the thigh and the leg. Other types of splint may further be contemplated.

This splint consists of two rigid and longilinear rods 12 which extend along the leg of the user U.

These rods 12 are adjustable and comprise adjustment means 60 in height for adjusting the height of the splint according to the size of the user.

In this example and as illustrated in FIG. 4, these adjustment means 60 consist in a slider mechanism 62 allowing sliding of the rods 12 for adjusting the height and a set of screws 61 allowing blocking in position of the rods, once the height is adjusted.

It is therefore sufficient for the user U to position his/her leg in the splint after having adjusted beforehand the height of the splint if required.

As illustrated in FIG. 6, the splint comprises immobilization means 11, for example a set of straps, for immobilizing the lower limb of the user U when the knee is in extension.

One skilled in the art will understand here that it is possible to contemplate means other than the straps for immobilizing the lower limb.

Once in position, the user U with the knee in extension may tighten the straps for immobilizing his/her lower limb.

In the example described here, the ergometer 100 comprises a second portion 20, also called a 3D force platform.

In this example, this second portion 20 comprises a main body 21 attached to the first portion 10. This main body 21 encompasses the foot of the user U.

As illustrated in FIG. 5, this second portion 20 comprises a counter-supporting element 22.

This counter-supporting element 22 consists in a plate secured to the main body 21.

Those skilled in the art will understand here that the counter-supporting element 22 and the main body 21 may form a single and same single piece part, for example obtained by molding.

In the example described here, and as illustrated in FIG. 5, the second portion 20 also comprises another rigid plate 23 which forms a supporting surface for the lower surface of the foot of the user U when the lower limb is immobilized by the splint with the immobilization means 11.

In the example described here and illustrated in FIG. 5, this plate 23 is substantially parallel to the counter-supporting element 22.

In this example, the plate 23 is fixed relatively to the counter-supporting element 22.

Thus, this plate 23 is static; i.e. it does not move and does not deform, from a macroscopic point of view, relatively to the counter-supporting element 22, even when the foot of the user exerts a force on said plate 23.

In order to further limit any deformation, the plate 23 has on its lateral edges stiffening elements 23a and 23b (see FIG. 5).

Between this plate 23 and the counter-supporting element 22, a force sensor 24 is inserted.

The layout of such a force sensor 24 inserted between the counter-supporting element 22 and the plate 23 is characteristic of the present invention.

Indeed, when the user U exerts a force on the plate 23 via his/her foot, this force is transmitted from the plate 23 to the counter-supporting element 22.

The force sensor 24 positioned between both elements 22 and 23 may then measure this transmitted force.

In this example, the sensor 24 is a 3D force sensor which contains a force-torque sensor of the type SH100D1002A2-2 from Sensix.

Such a force sensor 24 gives the possibility of measuring the forces during plantar flexion and during dorsal flexion.

It is provided that the foot of the user U be accommodated in a shoe 25 securely attached on the supporting surface of the plate 23.

In a complementary way, it is also possible to provide a set of straps 26 such as for example:
- two re-positionable self-adhesive attachment strips for maintaining the foot of the user U in position,
- other complementary re-positionable self-adhesive attachment strips attached on the force platform for blocking the movement of the ankle, one passing at the rear of the heel, the other one passing on the front of the joint of the ankle.

It is further possible to provide another re-positionable self-adhesive attachment strip placed at the dorsal face of the metatarsophalangeal joint in order to block any movement of the forefoot.

Once the set of these immobilization elements are positioned, the foot of the user U is secured to the supporting surface of the plate 23: in this configuration, the foot of the user U is firmly maintained in place with a shoe 25 attached to the plate 23, this plate 23 being itself attached on the force platform.

As illustrated in FIG. 6, the ergometer 100 according to the present invention is therefore used in the sitting position (or in the lying position), the lower limb of the user U being placed in the splint with the knee in extension and the foot fixed in the shoe 25 being securely attached to the platform of the ergometer 100.

Preferably, the axis of rotation of the ankle is aligned with the axis of the ergometer.

The leg is in extension at the joint of the knee and the joint of the ankle is in a neutral position: the longitudinal axis of the foot forms an angle of 90° with that of the leg in the sagittal plane, as this may be during the maintaining of the orthostatic position.

It is however possible to adjust the angular tilt of the joint of the ankle.

This is made possible by means of angular adjustment 50 which give the possibility of adjusting the angle formed by the axis of the foot P and that of the leg J.

As illustrated in FIGS. 4 and 5, these adjustment means 50 consist in a set of retractable nuts 51 positioned at the lower portion of the rods 12, the rods being attached to the main body 21 through a pivot.

The main body 21 has adjustment holes 52 for introducing said nuts 51.

By selecting the adjustment hole 52, it is possible for the user U to adjust the tilt of his/her foot relatively to the axis of his/her leg.

In the example described here, the ergometer is used in "an open chain".

According to this configuration, the heel of the boot (i.e. the heel of the second portion) comprises a rolling member 40.

In this example, the member 40 is formed by a plank 41 directly attached or indirectly attached to the heel of the boot (i.e. to the rear of the main body 21).

This plank 41 is itself placed on a rolling track 30 formed here by another plank 31. In this example, this plank 31 has on its contact surface with the plank 41 roller beads 32.

The relative displacement of the plank 41 on the beads 32 gives the possibility of making negligible any friction between the ergometer 100 and the support.

It will be understood here that other means are possible for avoiding such friction, like for example the presence of a roller on the heel of the boot.

In the described example, a cable 24a connecting the force sensor 24 of the ergometer to a computer processing unit (not shown here) is provided for carrying out the acquisitions.

The signals of forces measured by the sensor 24 are then sent through this cable 24a to the processing unit.

Alternatively, it may be provided that these signals are sent through wireless communication means.

These signals are then directly recorded by a processing piece of computing software of the type LABVIEW SIGNAL EXPRESS or MATLAB, with for example a sampling frequency of 100 Hz.

In the example described here, this processing unit includes a processor which may be configured for conducting isometric maximum force tests or for carrying out adapted exercises for rehabilitation.

For example, such a processor may be configured for requesting to the user to achieve explosive contractions (rapid rises with force) and then contractions carried out gradually over 5 seconds up to the maximum intensity (ramp condition: here it is for example possible to use a metronome beating at 60 bpm so that the subject achieves a regular rise in force over 5 seconds).

The processing unit may be connected to a display module (not shown here) for a representation of these objects to attain and viewing in real time the forces provided by the muscles, for example in the form of a graph representing in real time the measured force and the goal to be reached.

This display module thus gives the possibility to the user of controlling the efforts to be provided for example when this is an exercise where the target forces determined beforehand have to be attained.

The ergometer 100 according to the present invention thus appears like an apparatus for evaluating a goal giving the possibility, by means of the presence of a 3D force sensor 24 inserted between a supporting plate 23 which is free and a plate 22 used as a counter-support, the accurate and reliable measurement of the forces exerted on the joint of the ankle by the peri-articular muscles.

Such an ergometer 100 thus appears like a reliable, accurate measurement apparatus and affordable financially; it is moreover easy to transport, which provides the possibility of bringing the measurement instrument to the user (for example as far as his/her bed), and not the opposite as this is generally the case with existing ergometers.

It may therefore be easily transported, which is very appreciable if the intention is for example to test patients, and notably elderly persons or persons suffering from chronic instability of the ankle, who remain difficult to displace.

In the same way, it is possible to transport it into centers or rooms or sports fields for sportsmen in order to be used during training or physical preparation.

Moreover, in addition to the advantages above, it is possible to conduct measurements simultaneously on the two lower limbs by using two ergometers. This is referred to as a bilateral test.

Indeed it is known that the sum of the maximum forces simultaneously exerted by each of the muscles of both lower limbs during bilateral contraction is smaller than the sum of the maximum forces exerted during one-side contractions produced by these same muscles.

This is known under the term of bilateral deficiency.

The simultaneous use of two ergometers 100 according to the invention for a bilateral test shows this bilateral deficiency, when the ergometers are used in a "closed chain" configuration; i.e. by being supported against an abutment.

However, in the "open chain" configuration, such a bilateral deficiency is not again found.

The "closed chain" configuration gives the possibility, during one-sided contractions of using the postural adjustments for pushing more strongly, which is not possible in an "open chain" configuration.

During a bilateral thrust in "an open chain", the postural adjustments are not possible and the force measured by each ergometer 100 only corresponds to the force developed by the plantar flexor or dorsal flexor muscles of the ankle.

Thus, these bilateral tests with two ergometers 100 used simultaneously give the possibility of showing that no bilateral deficiency actually exists, but there rather exists a unilateral facilitation in a closed chain. In other words, whether this is in a one-sided or two-sided condition, the force developed at each ankle remains identical, which confirms the absence of a bilateral deficiency.

It should be observed that this detailed description deals with a particular exemplary embodiment of the present invention, but by no means this description has any limiting nature for the object of the invention; quite on the contrary, it has the goal of removing any possible uncertainty or any poor interpretation of the claims which follow.

The invention claimed is:

1. An ergometer (100) for measuring a force exerted on the joint of the ankle (C) of a lower limb of a user (U) by flexor muscles involved in the mobility of said ankle (C), configured to be used in a sitting position of the user (U), said ergometer (100) including:
    a first portion (10) comprising a splint able to receive said lower limb when the knee of said user (U) is in extension, and comprising a set of straps (11) configured for immobilizing said lower limb with the knee in extension and limiting flexion of the knee, and,
    a second portion (20) comprising:
        a) a main body (21) attached to the first portion (10),
        b) a counter-supporting plate (22) secured to said main body (21),
        c) a rigid plate (23) forming a supporting surface for the lower surface of the foot of the user when said lower limb is immobilized with the set of straps (11), said rigid plate (23) being substantially static relative to said counter-supporting plate (22),
        d) a force sensor (24) inserted between said plate (23) and said counter-supporting plate (22),
        e) a rolling or sliding track (30) comprising a plank (31) having a plurality of beads (32) distributed uniformly over said plank (31), and
        f) a rolling or sliding member (40) comprising a planar contact surface (41), directly or indirectly attached to the main body (21), said rolling or sliding member (40) being able to cooperate with said track (30) in order to limit the friction between said main body (21) and said track (30),
    said plate (23) being indirectly secured to said main body (21), said ergometer (100) being configured so that said force sensor (24) is able to measure the force exerted on the supporting surface of the plate (23) by the flexor muscles of the foot of the user involved in the mobility of said ankle (C), said force being transmitted from the plate (23) to the counter-supporting plate (22) with limited interference by the muscles participating in the flexion of the knee, whose flexion is limited due to its immobilization by said first portion (10).

2. The ergometer (100) according to claim 1, wherein the force sensor (24) is a 3D sensor for measuring a force exerted during plantar flexion and/or dorsal flexion of the foot of the user (U).

3. The ergometer (100) according to claim 2, wherein said force sensor (24) is a force moment sensor, able to measure the forces and the force moments in three dimensions.

4. The ergometer (100) according to claim 1, wherein said plate (23) comprises at its lateral edges stiffening elements (23a, 23b), each one comprising a plate which extends perpendicularly relative to said plate (23).

5. The ergometer (100) according to claim 1, wherein the second portion (20) comprises a shoe (25) for receiving the foot of the user (U), said shoe (25) being attached on the plate (23) so as to maintain said foot of the user (U) secured with said plate (23).

6. The ergometer (100) according to claim 1, further including first adjustment means (50), configured for adjusting the angular position of the second portion (20) relative to the first portion (10).

7. The ergometer (100) according to claim 6, wherein the first adjustment means (50) comprise:
    a pair of retractable nuts (51) positioned on the first portion (10), and
    a plurality of adjustment holes (52) made on the main body (21) of the second portion (20), said nuts (51) being able to be introduced into the adjustment holes (52) for the adjustment and the locking of the angular position of the second portion (20) relative to the first portion (10).

8. The ergometer (100) according to claim 1, further including second adjustment means (60), configured for adjusting the position of the first portion (10) relative to the second portion (20).

9. The ergometer (100) according to claim 1, including a computer processing unit including a processor able to receive and treat measurement signals from said sensor (24) in order to determine the force exerted by the flexor muscles of the foot of the user.

10. A method for conducting force tests on a patient in order to evaluate the capability of the patient of maintaining an orthostatic posture, the method comprising providing the ergometer of claim 1, and having the patient use the ergometer to evaluate said capability.

11. The ergometer (100) according to claim 2, wherein said plate (23) comprises at its lateral edges stiffening elements (23*a*, 23*b*), each one comprising a plate which extends perpendicularly relative to said plate (23).

12. The ergometer (100) according to claim 3, wherein said plate (23) comprises at its lateral edges stiffening elements (23*a*, 23*b*), each one comprising a plate which extends perpendicularly relative to said plate (23).

* * * * *